United States Patent [19]

Berg et al.

[11] Patent Number: 4,642,167
[45] Date of Patent: * Feb. 10, 1987

[54] SEPARATION OF ISOBUTYL ACETATE FROM ISOBUTANOL BY EXTRACTIVE DISTILLATION

[76] Inventors: Lloyd Berg, 1314 S. 3rd Ave.; An-I Yeh, 709 S. 12th Ave., both of Bozeman, Mont. 59715

[*] Notice: The portion of the term of this patent subsequent to Mar. 26, 2002 has been disclaimed.

[21] Appl. No.: 709,415

[22] Filed: Mar. 7, 1985

[51] Int. Cl.$^4$ .............................................. B01D 3/40
[52] U.S. Cl. ....................................... 203/60; 203/18; 203/DIG. 21; 560/248
[58] Field of Search ........................ 203/50, 60, 14, 18, 203/57, 91, DIG. 21, DIG. 13; 568/594; 560/248

[56] References Cited

U.S. PATENT DOCUMENTS

| | | | |
|---|---|---|---|
| 1,854,385 | 4/1932 | Van Schaak, Jr. | 568/594 |
| 2,171,550 | 9/1939 | Gordon | 203/60 |
| 2,386,927 | 10/1945 | Boyd, Jr. | 203/60 |
| 2,570,205 | 10/1951 | Carlson et al. | 203/58 |
| 2,993,841 | 7/1961 | Sarno | 203/60 |
| 4,379,028 | 4/1983 | Berg et al. | 203/60 |
| 4,507,176 | 3/1985 | Berg et al. | 203/51 |

FOREIGN PATENT DOCUMENTS 0937550  9/1963  United Kingdom ............... 570/262

*Primary Examiner*—S. Leon Bashore
*Assistant Examiner*—V. Manoharan

[57] ABSTRACT

Isobutyl acetate cannot be completely removed from isobutyl acetate—isobutanol—water mixtures by distillation because of the presence of the minimum ternary azeotrope. Isobutyl acetate can be readily removed from mixtures containing it, isobutanol and water by using extractive distillation in which the extractive distillation agent is a higher boiling oxygenated, nitrogenous and/or sulfur containing organic compound or a mixture of these. Typical examples of effective agents are N,N-dimethylacetamide; dimethylformamide and dimethylsulfoxide; acetamide, dimethylformamide and dipropylene glycol.

2 Claims, No Drawings

SEPARATION OF ISOBUTYL ACETATE FROM ISOBUTANOL BY EXTRACTIVE DISTILLATION

FIELD OF THE INVENTION

This invention relates to a method for separating isobutyl acetate from isobutanol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the most volatile component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the commercially important ways to manufacture isobutyl acetate is by the catalytic esterification of isobutanol with acetic acid. Isobutyl acetate (b.p.=118° C.), isobutanol (b.p.=108.1° C.) and water (b.p.=100° C.) form a ternary azeotrope boiling at 86.8° C. containing 46.5 wt.% isobutyl acetate, 23.1 wt.% isobutanol and 30.4 wt.% water.

Isobutyl acetate also forms a binary azeotrope with isobutanol which boils at 107.4° C. and contains 45 wt.% isobutyl acetate, and a binary azeotrope with water boiling at 87.4° C. containing 83.5 wt.% isobutyl acetate. Isobutanol also forms a binary minimum azeotrope with water which boils at 89.8° C. and contains 67 wt.% isobutanol. Thus in the esterification of isobutanol with acetic acid to form isobutyl acetate and water, the rectification of this mixture has three binary and one ternary azeotrope to contend with, and yields the lowest boiling constituent, namely the isobutyl acetate—isobutanol—water ternary azeotrope. It is therefore impossible to produce isobutyl acetate from isobutanol and water mixtures by rectification because the lower boiling ternary azeotrope will always come off overhead as the initial product. Any mixture of isobutyl acetate, isobutanol and water subjected to rectification at one atmosphere pressure will produce an overhead product boiling at 86.8° C. and containing 46.5 wt.% isobutyl acetate, 23.1 wt.% isobutanol and 30.4 wt.% water. Extractive distillation would be an attractive method of effecting the separation of isobutyl acetate from isobutanol if agents can be found that (1) will break the isobutyl acetate—isobutanol—water azeotrope and (2) are easy to recover from the isobutanol, that is, form no azeotrope with isobutanol and boil sufficiently above isobutanol to make the separation by rectification possible with only a few theoretical plates.

Extractive distillation typically requires the addition of an equal amount to twice as much extractive agent as the isobutyl acetate—isobutanol—water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is to be done by azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with isobutanol otherwise it will form a two-phase azeotrope with the isobutanol in the recovery column and some other method of separation will have to be employed.

The breaking of this azeotrope by extractive distillation is a new concept. The closest application of the concept might be the breaking of the methyl acetate—methanol azeotrope reported by Yoshida & Oka in Japanese patent 54/119-411, Sept. 17, 1979 or the breaking of the acetone—methanol azeotrope reported by Berg & Yeh, U.S. Pat. No. 4,501,645, Feb. 16, 1985.

OBJECTIVE OF THE INVENTION

The object of this invention is to provide a process or method of extractive distillation that will enhance the relative volatility of isobutyl acetate from isobutanol in their separation in a rectification column. It is a further object of this invention to identify suitable extractive distillation agents which will eliminate the isobutyl acetate—isobutanol—water ternary azeotrope and make possible the production of pure isobutyl acetate and isobutanol by rectification. It is a further object of this invention to identify organic compounds which, in addition to the above constraints, are stable, can be separated from isobutanol by rectification with relatively few theoretical plates and can be recycled to the extractive distillation column and reused with little decomposition.

SUMMARY OF THE INVENTION

The objects of the invention are provided by a process for separating isobutyl acetate from isobutanol which entails the use of certain oxygenated, nitrogenous and/or sulfur containing organic compounds as the agent in extractive distillation.

DETAILED DESCRIPTION OF THE INVENTION

We have discovered that certain oxygenated, nitrogenous and/or sulfur containing organic compounds, some individually but principally as mixtures, will effectively negate the isobutyl acetate—isobutanol—water ternary azeotrope and permit the separation of pure isobutyl acetate from isobutanol by rectification when employed as the agent in extractive distillation. Table 1 lists the compounds, mixture and approximate proportions that we have found to be effective. The data in Table 1 was obtained in a vapor-liquid equilibrium still. In each case, the starting material was the isobutyl acetate—isobutanol—water azeotrope. The ratios are the parts by weight of extractive agent used per part of isobutyl acetate isobutanol—water azeotrope. The relative volatilities are listed for each of the two ratios employed. The compounds that are effective when used alone are ethylene glycol, propylene glycol, 1,4-butanediol, 1,5-pentanediol, 1,6-hexanediol, hexylene glycol, diethylene glycol, triethylene glycol, tetraethylene glycol, dipropylene glycol, polyethylene glycol and 1,2,6-hexanetriol. The compounds that are effective when used alone are acetamide, N,N-dimethylacetamide and dimethylsulfoxide. The compounds which are also effective when used in mixtures of two or more components are ethylene glycol, propylene glycol, 1,4-butanediol, 1,5-pentanediol, 1,6-hexanediol, hexylene glycol, diethylene glycol, triethylene glycol, dipropylene glycol, polyethylene glycol, polypropylene glycol, glycerine, 1,2,6-hexanetriol, ethylene carbonate and propylene carbonate.

TABLE 1

Extractive Distillation Agents That Are Effective In Separating Isobutyl acetate From Isobutanol Which Contain Amides

| Compounds | Ratios | | Relative Volatilities | |
|---|---|---|---|---|
| Acetamide | 1 | 6/5 | 2.14 | 1.62 |
| N,N—Dimethylacetamide | " | " | 1.49 | 1.69 |
| Dimethylformamide (DMFA), Ethylene glycol | $(1/2)^2$ | $(3/5)^2$ | 1.51 | 1.73 |
| DMFA, Propylene glycol | " | " | 1.46 | 1.46 |
| DMFA, 1,4-Butanediol | " | " | 1.70 | 1.69 |
| DMFA, 1,5-Pentanediol | " | " | 1.73 | |
| DMFA, 1,6-Hexanediol | " | " | 1.54 | 1.69 |
| DMFA, Hexylene glycol | " | " | 1.36 | 1.47 |
| DMFA, Diethylene glycol | " | " | 1.66 | 1.83 |
| DMFA, Triethylene glycol | " | " | 1.69 | 1.58 |
| DMFA, Dipropylene glycol | " | " | 1.48 | 1.49 |
| DMFA, Polyethylene glycol | " | " | 1.52 | 1.90 |
| DMFA, Polypropylene glycol | " | " | 1.23 | 1.33 |
| DMFA, Glycerine | " | " | 1.77 | 1.80 |
| DMFA, 1,2,6-Hexanetriol | " | " | 1.52 | 1.66 |
| DMFA, Acetamide | " | " | 1.57 | 1.93 |
| DMFA, N,N—Dimethylacetamide | " | " | 1.35 | 1.86 |
| DMFA, Ethylene carbonate | " | " | 1.43 | 1.41 |
| DMFA, Propylene carbonate | " | " | 1.19 | 1.18 |
| Acetamide, Propylene glycol | " | " | 1.69 | 1.84 |
| Acetamide, 1,4-Butanediol | " | " | 1.86 | 2.11 |
| Acetamide, 1,5-Pentanediol | " | " | 1.58 | 1.77 |
| Acetamide, 1,6-Hexanediol | " | " | 1.68 | 1.71 |
| N,N—Dimethylacetamide, 1,4-Butanediol | " | " | 1.67 | 1.90 |
| N,N—Dimethylacetamide, 1,6-Hexanediol | " | " | 1.62 | 1.42 |
| N,N—Dimethylacetamide, Glycerine | " | " | 1.84 | 1.92 |
| DMFA, Acetamide, Ethylene glycol | $(1/3)^3$ | $(2/5)^3$ | 2.09 | 1.79 |
| DMFA, Acetamide, Propylene glycol | " | " | 1.62 | 1.78 |
| DMFA, Acetamide, 1,4-Butanediol | " | " | 1.80 | 1.95 |
| DMFA, Acetamide, 1,5-Pentanediol | " | " | 1.78 | 1.83 |
| DMFA, Acetamide, 1,6-Hexanediol | " | " | 1.74 | 2.13 |
| DMFA, Acetamide, Hexylene glycol | " | " | 1.60 | 1.69 |
| DMFA, Acetamide, Diethylene glycol | " | " | 1.84 | 1.61 |
| DMFA, Acetamide, Triethylene glycol | " | " | 1.67 | 1.79 |
| DMFA, Acetamide, Dipropylene glycol | " | " | 1.74 | 2.04 |
| DMFA, Acetamide, Polyethylene glycol | " | " | 1.90 | 1.93 |
| DMFA, Acetamide, Polypropylene glycol | " | " | 1.53 | 1.53 |
| DMFA, Acetamide, Glycerine | " | " | 1.55 | 2.03 |
| DMFA, Acetamide, 1,2,6-Hexanetriol | " | " | 1.52 | 1.69 |
| DMFA, Acetamide, N,N—Dimethylacetamide | " | " | 2.00 | 1.99 |
| DMFA, Acetamide, Ethylene carbonate | " | " | 1.57 | 1.90 |
| DMFA, Acetamide, Propylene carbonate | " | " | 1.24 | 1.21 |
| Acetamide, N,N—Dimethylacetamide, Propylene glycol | " | " | 1.83 | 1.41 |
| Acetamide, N,N—Dimethylacetamide, 1,4-Butanediol | " | " | 2.08 | 1.52 |
| Acetamide, N,N—Dimethylacetamide, 1,6-Hexanediol | " | " | 1.50 | 1.60 |
| Acetamide, N,N—Dimethylacetamide, Glycerine | " | " | 1.95 | 2.08 |
| DMSO, Dimethylformamide | " | " | 2.05 | 2.32 |
| DMSO, Acetamide | " | " | 1.86 | 1.66 |
| DMSO, N,N—Dimethylacetamide | " | " | 2.21 | 2.20 |
| DMSO, Ethylene carbonate | " | " | 1.50 | 1.62 |
| DMSO, Propylene carbonate | " | " | 1.31 | 1.40 |
| DMSO, DMFA, Ethylene carbonate | " | " | 1.46 | 1.85 |
| DMSO, DMFA, Propylene carbonate | " | " | 1.56 | 1.57 |
| DMSO, DMFA, N,N—Dimethylacetamide | " | " | 2.18 | 2.22 |
| Dimethylsulfoxide (DMSO) | 1 | 6/5 | 1.71 | 2.29 |

Table 2 lists some single compounds and mixtures which are ineffective in separating isobutyl acetate from isobutanol.

on condensation, immediately forms two liquid layers. The solubility of isobutyl acetate in water is only 0.6%.

TABLE 2

Some Extractive Distillation Agents That Are Ineffective In Separating Isobutyl acetate From Isobutanol

| Compounds | Ratios | | Relative Volatilities | |
|---|---|---|---|---|
| Sulfolane | 1 | 6/5 | 0.93 | 1.07 |
| Ethylene carbonate | " | " | 0.57 | 0.82 |
| Propylene carbonate | " | " | 0.81 | 0.74 |
| Polypropylene glycol | " | " | 0.84 | 0.81 |
| Sulfolane, Ethylene carbonate | $(1/2)^2$ | $(3/5)^2$ | 0.88 | 0.91 |
| Sulfolane, Propylene carbonate | " | " | 0.88 | 0.89 |
| Ethylene carbonate, Propylene carbonate | " | " | 0.70 | 0.72 |
| Sulfolane, Propylene carbonate, Ethylene carbonate | $(1/3)^3$ | $(2/5)^3$ | 0.79 | 0.91 |
| Sulfolane, Ethylene carbonate, N—Methylpyrrolidone | " | " | 1.10 | 0.88 |

The two relative volatilities shown in Table 1 correspond to the two different ratios employed. For example, in Table 1, one part of N,N-dimethylacetamide with one part of isobutyl acetate—isobutanol—water azeotrope gives a relative volatility of 1.49, 6/5 parts of N,N-dimethylacetamide gives 1.69. One half part of DMFA mixed with one half part of ethylene glycol with one part of isobutyl acetate—isobutanol—water azeotrope gives a relative volatility of 1.51, 3/5 parts of DMFA plus 3/5 parts of ethylene glycol gives 1.73. One third parts of DMFA plus ⅓ parts of acetamide plus ⅓ parts of 1,4-butanediol mixed with one part of isobutyl acetate—isobutanol—water azeotrope gives a relative volatility of 1.80, with 2/5 parts, these three give 1.95. In every example in Table 1, the starting material is the isobutyl acetate—isobutanol—water azeotrope which possesses a relative volatility of 1.0.

Several of the compounds and mixtures listed in Table 1 and whose relative volatility has been determined in the vapor-liquid equilibrium still, were then evaluated in a glass perforated plate rectification column possessing 4.5 theoretical plates. The isobutyl acetate—isobutanol—water mixture studied contained 63.8 wt.% isobutyl acetate, 31.7 wt% isobutanol, 4.5 wt.% water. The isobutyl acetate—isobutanol—water azeotrope contains 46.5 wt.% isobutyl acetate, 23.1 wt.% isobutanol and 30.4 wt.% water. In every case, the overhead was richer than 46.5 wt.% isobutyl acetate and the results are tabulated in Table 3. Without the extractive agent, the overhead would be the azeotrope, 46.5 wt.% isobutyl acetate. This proves that the extractive agent is negating the azeotrope and makes rectification proceed as if the azeotrope no longer exists and brings the more volatile components, isobutyl acetate and water, out as the overhead products. It is our belief that this is the first time that this has been accomplished for this azeotrope.

The data in Table 3 was obtained in the following manner. The charge was 63.8 wt.% isobutyl acetate, 31.7 wt.% isobutanol and 4.5 wt.% water and after a half hour of operation in the 4.5 theoretical plate column to establish equilibrium, dimethylformamide at 75° C. and 20 ml/min. was pumped in. The rectification was continued for two hours with sampling of overhead and bottoms after one hour, 1.5 hours and two hours. The average of the three analyses was 97.88 wt.% isobutyl acetate in the overhead and 54.1 wt.% in the bottoms, both on a water-free basis which gives a relative volatility of 2.26 of isobutyl acetate to isobutanol. This indicates that the ternary azeotrope has been negated and separation accomplished. The isobutyl acetate comes off in the form of its binary azeotrope with water which

TABLE 3

Data From Runs Made In Rectification Column.

| Agent | Relative Volatility |
|---|---|
| Dimethylsulfoxide (DMSO) | 2.61 |
| Dimethylformamide (DMFA) | 2.26 |
| Ethylene glycol | 2.89 |
| Propylene glycol | 2.24 |
| Diethylene glycol | 1.51 |
| 1,4-Butanediol | 1.87 |
| Triethylene glycol | 1.43 |
| Dipropylene glycol | 1.41 |
| Tetraethylene glycol | 1.36 |
| DMSO + DMFA | 2.12 |
| DMFA + Ethylene glycol (1:1) | 1.69 |
| Ethylene glycol + Acetamide (4:1) | 2.06 |
| DMSO + Acetamide (1:1) | 1.68 |
| DMSO (R) + DMFA (R) + Ethylene glycol (1:1:1) | 2.02 |

Mixture: 255 gm. Isobutyl acetate + 127 gm. Isobutanol + 18 gm. Water
Agents: Added at 75° C. and 20 ml/min.
(R): Reclaimed and re-used
Numbers in (-) indicate the weight ratio of the agents

THE USEFULNESS OF THE INVENTION

The usefulness or utility of this invention can be demonstrated by referring to the data presented in Tables 1–3. All of the successful extractive distillation agents show that isobutyl acetate, isobutanol and water can be separated from their ternary azeotrope by means of distillation in a rectification column and that the ease of separation as measured by relative volatility is considerable. Without these extractive distillation agents, no improvement above the azeotrope composition will occur in a rectification column. The data also show that the most attractive agents will operate at a boilup rate low enough to make this a useful and effecient method of recovering high purity isobutyl acetate from any mixture of these three including the ternary minimum azeotrope. The stability of the compounds used and the boiling point difference is such that complete recovery and recycle is obtainable by a simple distillation and the amount required for make-up is small.

WORKING EXAMPLES

EXAMPLE 1

The isobutyl acetate—isobutanol—water azeotrope is 46.5 wt.% isobutyl acetate, 23.1 wt.% isobutanol, 30.4 wt.% water. Fifty grams of the isobutyl acetate—isobutanol—water azeotrope and fifty grams of N,N-dimethylacetamide were charged to an Othmer type glass vapor-liquid equilibrium still and refluxed for twelve hours. Analysis of the vapor and liquid by gas chromatography gave vapor of 64% isobutyl acetate, 36% isobutanol; liquid of 54.4% isobutyl acetate, 45.6% isobutanol. This indicates a relative volatility of 1.49. Ten grams of ethylene glycol were added and refluxing continued for another twelve hours. Analysis indicated a vapor composition of 67.8% isobutyl acetate, 32.2% isobutanol; a liquid composition of 50% isobutyl acetate, 50% isobutanol which is a relative volatility of 1.69.

EXAMPLE 2

Fifty grams of the isobutyl acetate—isobutanol—water azeotrope, 25 grams of acetamide and 25 grams of DMFA were charged to the vapor-liquid equilibrium still and refluxed for twelve hours. Analysis indicated a vapor composition of 62.7% isobutyl acetate, 37.3% isobutanol; a liquid composition of 51.7% isobutyl acetate, 48.3% isobutanol which is a relative volatility of 1.57. Five grams of acetamide and five grams of DMFA were added and refluxing continued for another eleven hours. Analysis indicated a vapor composition of 65.2% isobutyl acetate, 34.8% isobutanol; a liquid composition of 49.2% isobutyl acetate, 50.8% isobutanol which is a relative volatility of 1.93.

EXAMPLE 3

Fifty grams of the isobutyl acetate—isobutanol—water azeotrope, 17 grams of dipropylene glycol, 17 grams of acetamide and 17 grams of DMFA were charged to the vapor-liquid equilibrium still and refluxed for thirteen hours. Analysis indicated a vapor composition of 64.8% isobutyl acetate, 35.2% isobutanol; a liquid composition of 51.3% isobutyl acetate, 48.7% isobutanol which is a relative volatility of 1.74. Three grams each of dipropylene glycol, acetamide and DMFA were added and refluxing continued for another ten hours. Analysis indicated a vapor composition of 63.8% isobutyl acetate, 36.2% isobutanol; a liquid composition of 46.4% isobutyl acetate, 53.6% isobutanol which is a relative volatility of 2.04.

EXAMPLE 4

A glass perforated plate rectification column was calibrated with ethylbenzene and p-xylene which possesses a relative volatility of 1.06 and found to have 4.5 theoretical plates. A solution of 255 grams of isobutyl acetate, 127 grams of isobutanol and 18 grams of water was placed in the stillpot and heated. When refluxing began, an extractive agent comprising dimethylformamide was pumped into the column at a rate of 20 ml/min. The temperature of the extractive agent as it entered the column was 75° C. After establishing the feed rate of the extractive agent, the heat input to the isobutyl acetate, isobutanol and water in the stillpot was adjusted to give a total reflux of 10–20 ml/min. After one hour of operation, the overhead and bottoms samples of approximately two ml. were collected and analysed using gas chromatography. The overhead analysis was 97.94% isobutyl acetate, 2.06% isobutanol. The bottoms analysis was 53.99% isobutyl acetate, 46.01% isobutanol. Using these compositions in the Fenske equation, with the number of theoretical plates in the column being 4.5, gave an average relative volatility of 2.27 for each theoretical plate. After 1½ hours of total operating time, the overhead and bottoms samples were taken again and analysed. The overhead composition was 97.86% isobutyl acetate, 2.14% isobutanol and the bottoms composition was 54.02% isobutyl acetate, 45.98% isobutanol. This gave an average relative volatility of 2.26 for each theoretical plate. After two hours of total operating time, the overhead and bottoms samples were again taken and analysed. The overhead composition was 97.85% isobutyl acetate, 2.14% isobutanol and the bottoms composition was 54.0% isobutyl acetate, 46.0% isobutanol. This gave an average relative volatility of 2.25 for each theoretical plate.

EXAMPLE 5

A solution of 255 grams of isobutyl acetate, 127 grams of isobutanol and 18 grams of water was placed in the stillpot of the same column used in Example 4 and heat applied. When refluxing began, an extractive agent comprising 50% DMFA and 50% DMSO was fed into the top of the column at a feed rate of 20 ml/min. and a temperature of 75° C. After establishing the feed rate of the extractive agent, the heat input to the isobutyl acetate, isobutanol and water in the stillpot was adjusted to give a total reflux rate of 10–20 ml/min. Having established the reflux rate, the column was allowed to operate for one hour. After one hour of steady operation, overhead and bottoms samples of approximately two ml. were collected and analysed using gas chromatography. The overhead analysis was 96.82% isobutyl acetate, 3.18% isobutanol, the bottoms analysis was 56.11% isobutyl acetate, 43.89% isobutanol. Using these compositions in the Fenske equation with the number of theoretical plates in the column being 4.5, gave an average relative volatility of 2.02 for each theoretical plate. After 1½ hours of total operation, the overhead composition was 97.74% isobutyl acetate, 2.26% isobutanol and the bottoms composition was 57.33% isobutyl acetate, 42.67% isobutanol. This gave an average relative volatility of 2.16 for each theoretical plate. After two hours of total operation, the overhead composition was 97.47% isobutyl acetate, 2.53% isobutanol and the bottoms composition was 56.27% isobutyl acetate, 43.73% isobutanol. This gave an average relative volatility of 2.12 for each theoretical plate.

The nature of the present invention having been described, what we wish to claim as new and useful and secure by Letters Patent is:

1. A method for recovering isobutyl acetate from a mixture of isobutyl acetate, isobutanol and water which comprises distilling a mixture of isobutyl acetate, isobutanol and water in a rectification column in the presence of extractive agent, recovering isobutyl acetate and water as overhead product and obtaining the extractive agent and isobutanol from the bottoms of the rectification column, the extractive agent comprises N,N-dimethylacetamide.

2. A method for recovering isobutyl acetate from a mixture of isobutyl acetate, isobutanol and water which comprises distilling a mixture of isobutyl acetate, isobutanol and water in a rectification column in the presence of extractive agent, recovering isobutyl acetate and water as overhead product and obtaining the extractive agent and isobutanol from the bottoms of the rectification column, the extractive agent comprises acetamide.

* * * * *